United States Patent

Nakazato et al.

Patent Number: 5,116,995
Date of Patent: May 26, 1992

[54] CARBAZOLE COMPOUNDS

[75] Inventors: Atsuro Nakazato, Satte; Sanae Kitsukawa, Tokyo; Yutaka Kawashima, Tatebayashi; Katsuo Hatayama, Omiya; Satoshi Hibino, Fukuyama, all of Japan

[73] Assignee: Taisho Pharmaceutical Co., Ltd., Japan

[21] Appl. No.: 702,507

[22] Filed: May 20, 1991

[30] Foreign Application Priority Data

May 25, 1990 [JP] Japan ................... 2-135838

[51] Int. Cl.⁵ .......................... C07D 209/86
[52] U.S. Cl. .................... 548/444; 548/441
[58] Field of Search ................ 548/441, 444

[56] References Cited

U.S. PATENT DOCUMENTS 3,833,596 9/1974 Albrecht et al. ............... 548/444

Primary Examiner—Robert W. Ramsuer
Attorney, Agent, or Firm—Lorusso & Loud

[57] ABSTRACT

Carbazole compounds represented by the formula

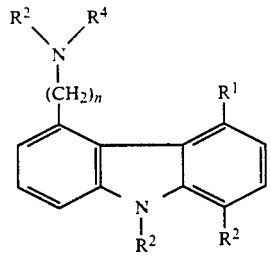

wherein $R^1$ is a hydrogen atom or an alkyl group having 1 to 5 carbon atoms, $R^2$ is a hydrogen atom, an alkyl group having 1 to 5 carbon atoms, an alkanoyl group having 2 to 6 carbon atoms or a benzoyl group, $R^3$ and $R^4$ are the same or different, and are each hydrogen atom, an alkyl group having 1 to 7 carbon atoms, an alkenyl group having 2 to 4 carbon atoms, an alkyl group having 1 to 3 carbon atoms substituted by a phenyl group, or $R^3$ and $R^4$ together with the nitrogen atom to which they are attached form a morpholino group, a piperidino group, a pyrrolidino group or a piperazino group, and n is an integer from 1 to 3, and salts thereof have strong antipsychotic activity.

3 Claims, No Drawings

CARBAZOLE COMPOUNDS

BACKGROUND OF THE INVENTION (1) Field of the invention

The present invention relates to carbazole compounds having antipsychotic action.

(2) Prior Art

Antipsychotic drugs are used not only for the treatment of schizophrenia but also for the treatment of the problem behaviors (e.g. aggressive behavior, excitation, poriomania and delirium) accompanied by cerebrovascular diseases and senile dementia. However, there is a serious problem that prior antipsychotic drugs induce strong extrapyramidal tract injury as a side effect. In order to solve such a problem, recent antipsychotic drugs are being developed by approaching to the reaction mechanism which is different from that of the prior drugs. Among these drugs are sigma receptor antagonists. The sigma receptor is considered to participate alienation such as hallucina. The compounds which have a specific affinity for the receptor have antipsychotic action without showing extraphramidal tract injury. As an example of such compounds is known rimcazole, but, of which affinity and specificity for sigma receptor are not sufficient.

As a result of earnest researches to compounds having a carbazole skeleton, the present inventors have found novel carbazole compounds having specific and strong affinity for sigma receptor without extrapyramidal tract injury, and have accomplished the present invention.

SUMMARY OF THE INVENTION

An object of the present invention is to provide a carbazole compound represented by the formula

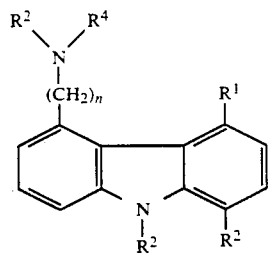

I wherein $R^1$ is a hydrogen atom or an alkyl group having 1 to 5 carbon atoms, $R^2$ is a hydrogen atom, an alkyl group having 1 to 5 carbon atoms, an alkanoyl group having 2 to 6 carbon atoms or a benzoyl group. $R^3$ and $R^4$ are the same or different, and are each a hydrogen atom, an alkyl group having 1 to 7 carbon atoms, an alkenyl group having 2 to 4 carbon atoms, an alkyl group having 1 to 3 carbon atoms substituted by a phenyl group, or $R^3$ and $R^4$ together with the nitrogen atom to which they are attached form a morpholino group, a piperidino group, a pyrrolidino group or a piperazino group, and n is an integer from 1 to 3, or a salt thereof.

DETAILED DESCRIPTION OF THE INVENTION

In the present invention, the alkyl group having 1 to 5 carbon atoms refers to a straight or branched chain alkyl group such as, for example, a methyl group, an ethyl group, a propyl group, an isopropyl group, a butyl group, an isobutyl group and a pentyl group. The alkyl group having 1 to 7 carbon atoms refers to a straight or branched chain alkyl group such as, for example, those given above, a hexyl group and a heptyl group. The alkyl group having 1 to 3 carbon atoms substituted by a phenyl group refers to a straight or branched chain alkyl group substituted by a phenyl group at any available position such as, for example, benzyl group, phenethyl group and phenylpropyl group. The alkenyl group having 2 to 4 carbon atoms refers to a straight or branched chain alkenyl group such as, for example, a vinyl group, an allyl group and a propenyl group. The alkanoyl group having two to 6 carbon atoms refers to a straight or branched chain alkanoyl group such as, for example, an acetyl group, a propionyl group, a butyryl group and valeryl group. The salt of the compound of the present invention refers to a pharmaceutically acceptable salt thereof, for example, salts with mineral acids (e.g. sulfuric acid, hydrochloric acid and phosphoric acid) and organic acids (e.g. acetic acid, lactic acid, tartaric acid, fumaric acid, maleic acid, trifluoroacetic acid and methanesulfonic acid).

Among preferred compounds of the present invention are 5,8-dimethyl-4-(di-n-propylaminomethyl)-carbazole hydrochloride and 5,8-dimethyl-4-(2-di-n-propylaminoethyl)carbazole hydrochloride.

The compound of Formula I wherein $R^2$ is a hydrogen atom can be prepared according to the following reaction schemes in which R is a lower alkyl group, X is a halogen atom. Y is a protective group, and $R^1$, $R^3$ and $R^4$ are as defined above.

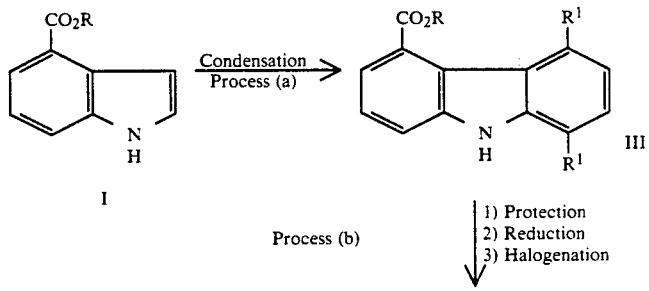

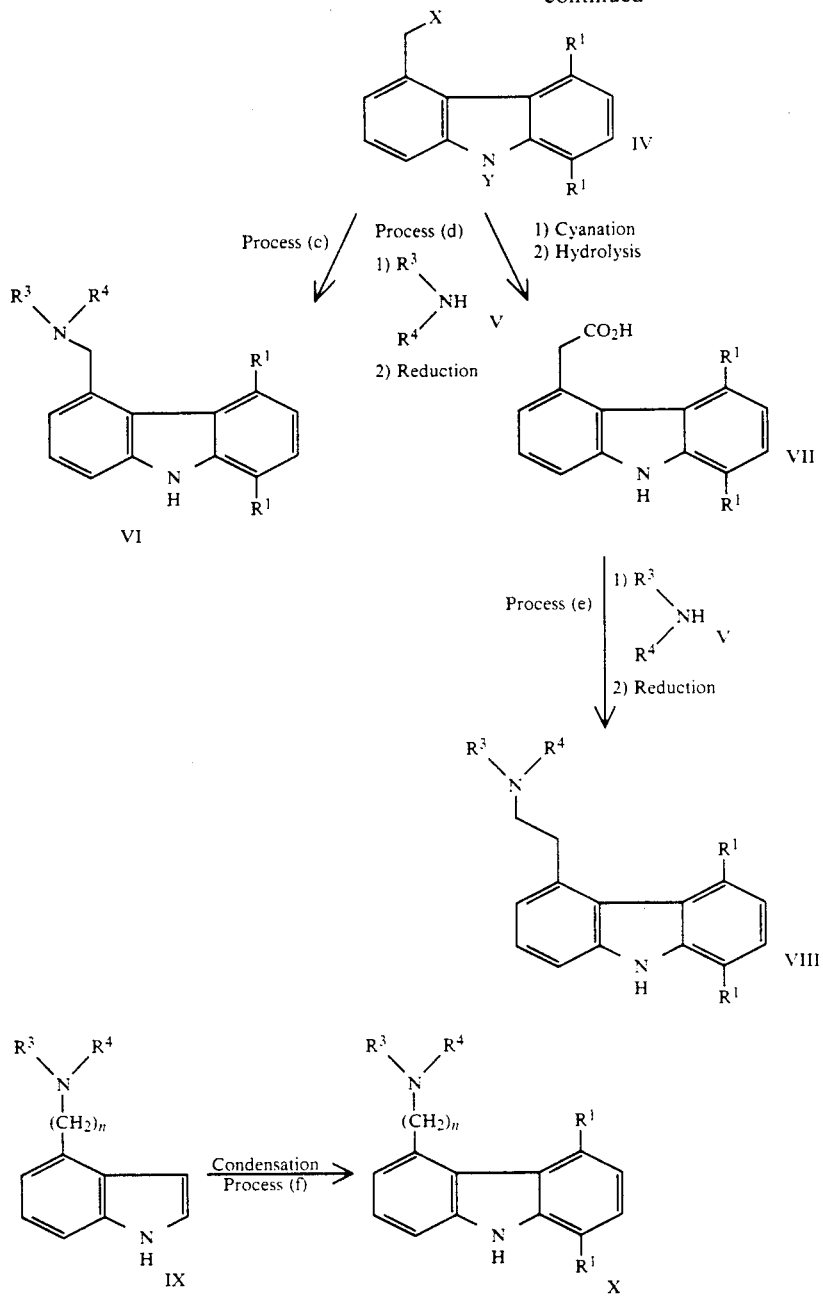

Process (a): An indole compound of Formula II known in J. Org. Chem., vol. 44, page 4003 (1979), is condensed with acetonylacetone or 2,5-dimethoxytetrahydrofuran in the presence of a catalyst in a reaction-inert solvent to give a compound of Formula III. Examples of the catalyst used in the reaction are organic acids such as trifluoroacetic acid and p-toluenesulfonic acid, or inorganic acids such as hydrochloric acid and sulfonic acid. Examples of the solvent are alcohols (e.g. ethanol), ethers (e.g. dioxane and 1,2-dimethoxyethane), benzene and toluene. The reaction is carried out with stirring at 50 to 150° C. for 3 to 20 hours, preferably at 70 to 120° C. for 8 to 11 hours.

Process (b): The compound of Formula III is subjected to protection of the NH group with, for example, a p-toluene-sulfonyl group and a benzenesulfonyl group; reduction of the ester group; and halogenation to give a compound of formula IV. The protection in this process is carried out by using a protective agent (e.g. p-toluenesulfonyl chloride and benzenesulfonyl chloride) in the presence of a base (e.g. sodium hydride) in a solvent (e.g. N,N-dimethylformamide, dimethyl sulfoxide, toluene and tetrahydrofuran) with stirring at 0 to 150° C. for two to 24 hours, preferably at 0° C. to room temperature overnight. The reduction is carried out by using a reducing agent such as aluminum series reducing agents (e.g. aluminum lithium hydride), and boron series reducing agents (e.g. lithium borohydride) in a solvent (e.g. tetrahydrofuran, 1,2-dimethoxyethane and toluene) with stirring at 0° C. to room temperature for two to 5 hours. The halogenation is carried out by using a halogenating agent (e.g. triphenyl-phosphine - carbon tetrachloride, triphenylphcsphine -carbon tetrabromide, thionyl chloride, phosphorus oxychloride, phosphorus oxybromide and phosphorus penta-chloride) in a solvent (e.g. dichloromethane, chloroform, tetrahydrofuran, N,N-dimethylformamide and hexamethyl-Phosphoric triamide) with stirring at 0 to 100° C. for one to 24 hours, preferably at room temperature overnight.

Process (c): The compound of Formula IV is allowed to react with an amine of Formula V, and hydrolyzed to give the compound of Formula VI of the present invention. The reaction with the amine is carried out by using a base such as inorganic bases (e.g. potassium carbonate and sodium carbonate) and tertiary amines (e.g. triethylamine, N-methylmorpholine and N,N-dimethylaniline) and an amine of Formula V in a solvent (e.g. acetonitrile, methanol, ethanol, isopropanol, toluene, benzene, tetrahydrofuran, dioxane, N,N-dimethylformamide and dimethyl sulfoxide) with stirring at 50 to 150° C. for 5 to 24 hours. The hydrolysis is carried out by using a base (e.g. sodium hydroxide, potassium hydroxide, lithium hydroxide and calcium hydroxide) in a mixture of water and an organic solvent such as alcohols (e.g. ethanol), ethers (e.g. dioxane and 1,2-dimethoxyethane) and N,N-dimethyl-formamide, with stirring at reflux for 10 to 17 hours.

Process (d): The compound of Formula IV is subjected to cyanation and hydrolysis to give a compound of Formula VII. The cyanation is carried out by using a cyaniting agent (e.g. potassium cyanide, sodium cyanide and copper cyanide) in the absence or presence of a catalyst. Examples of the catalyst are crown ethers (e.g. 18-crown-6), phase-transfer catalysts (e.g. tetrabutylammonium chloride). In the cyanation, there is used a solvent (e.g. acetonitrile, benzene, toluene, chloroform, tetrahydrofuran, N,N-dimethylformamide and dimethyl sulfoxide; alone or in admixture with water). The reaction is carried out with stirring at room temperature to 150° C. overnight. The hydrolysis is carried out by using a base (e.g. sodium hydroxide, potassium hydroxide, lithium hydroxide and calcium hydroxide) in a mixture of water and an organic solvent such as alcohols (e.g. ethanol), ethers (e.g. dioxane and 1,2-dimethoxyethane) and N,N-dimethylformamide, with stirring at reflux for 10 to 17 hours.

Process (e): The compound of Formula VII is activated by conversion of the carboxyl group into a mixed acid anhydride or an acid halide, and amidated with an amine of Formula V, followed by hydrolysis to give the compound of the present invention. The conversion into the mixed acid anhydride of the carboxyl group of Formula VII is carried out by reacting the compound of Formula VII with, for example, ethyl chlorocarbonate, isobutyl chlorocarbonate, acetic anhydride and acetic chloride in the presence of a base (e.g. triethylamine and N-methylmorpholine) in a solvent. Examples of the solvent used herein are tetrahydrofuran, dichloromethane, N,N-dimethylformamide and toluene. The reaction is carried out with stirring at −30° C. to room temperature for 10 to 40 minutes.

The conversion of the compound of Formula VII into the acid halide is carried out by reacting the compound of Formula VII with, for example, hexamethylphosphorous triamide - carbon tetrachloride, triphenylphosphine - carbon tetrachloride, thionyl chloride, Phosphorus oxychloride and phosphorus pentachloride in a solvent with stirring at room temperature for 30 minutes to 2 hours. Examples of the solvent used herein are tetrahydrofuran, dichloromethane, N,N-dimethylformamide, toluene and benzene.

The reduction is carried out by using a reducing agent (e.g. aluminum lithium hydride and borone·tetrahydrofuran complex) in a solvent (e.g. tetrahydrofuran, 1,2-dimethoxyethane and toluene) with stirring at 0 to 150° C. for one to 24 hours, preferably at room temperature to 80° C. for two to 10 hours.

Process (f): Alternatively, the compound of Formula X of the present invention can be prepared by condensing the compound of Formula IX [known in J. heterocyclic Chem., vol. 19, page 1195 (1982) or obtained by a process similar to the known process] with acetonylacetone or 2,5-dimethoxytetrahydrofuran according to a method similar to that of Process (a).

On the other hand, the compound of Formula I wherein $R^2$ is an alkyl group having one to 5 carbon atoms can be prepared by reacting a compound of Formula VI, VIII or X with a compound of the formula $R^2$-X' (wherein $R^2$ is as defined above, and X' is a halogen atom) in the presence of a base in a solvent. Examples of the base are sodium hydride, potassium hydride, sodium amide, potassium amide, sodium bis(trimethylsilyl)amide, potassium bis(trimethylsilyl)amide, potassium t-butoxide and sodium ethoxide, and examples of the solvent are N,N-dimethylformamide, dimethyl sulfoxide, tetrahydrofuran and 1,2-dimethoxyethane.

The compounds of the present invention show specific and strong affinity for sigma receptor, and have effect on inhibition of methamphetamine induced hyperlocomotion which is a screening test for the antipsychotic agents. Accordingly, the compounds of the present invention are useful antipsychotic agents without extrapyramidal tract injury. For these porposes, the compound of the present invention is mixed with suitable pharmaceutically acceptable carries for solid or liquid form to give the pharmaceutical preparation for oral or parenteral administration. Examples of the pharmaceutical preparation are solid forms such as tablets, pills, capsules and granules, liquid forms such as injec'tional solutions, and external forms such as ointments and suppositories, all of which can be prepared according to conventional pharmaceutical prectices. The carriers in the above-mentioned preparations can include ordinary additives such as auxiliaries, stabilizers, wetting agents and emulsifiers. For example, there can be used solubilizers (e.g. injectional distilled water, physiological saline solution and Ringer's solution) and preservers (e.g. methyl p-oxybenzolate and propyl p-oxybenzoate) for injectional solutions; and used sorbitol syrup, methylcellulose, glucose, sucrose syrup, hydroxyethylcellulose, food oil, glycerin, ethanol, water, emulsifiers (e.g. gum arabic and lecithin) and detergents (e.g. Tween and Span) for syrups and emulsions. Tor the solid forms, there can be used excipients (e.g. milk sugar, corn starch and mannitol), lubricants (e.g. calcium phosphate, magnesium stearate and talc), binders (e.g. sodium carboxymethylcellulose and hydroxypropylcellulose), disintegraters (e.g. crystalline cellulose, calcium carboxymethylcellulose) and fluid accelerators (e.g. light silicic anhydride).

The dosage of the compound of the invention to a patient depends of the age of the patient, the kind and conditions of the discase, but usually it is from 0.5 to 20 mg in single or several divided doses per adult per day.

Experiments are illustrated as follows.

EXPERIMENT 1

[Receptor Binding Test]

Male Wistar rats were used for the test. As [$^3$H]labelled ligands, (+)-[$^3$H]3-PPP [3-(3-hydroxyphenyl)-N-n-propylpiperidine]for sigma receptor, (−)-[$^3$H]sulpiride for D2 receptor and [$^3$H]phencyclidine for phencyclidine receptor were used.

The binding reactions using [$^3$H]labelled ligands were carried out according to the following methods (1) to (3) as described in Molecular Pharmacology, vol. 32, page 772 (1987), Journal of Pharmacy and Pharmacology, vol. 32, page 441 (1980), and Molecular Pharmacology, vol. 32, page 820 (1987), respectively.

(1) (−)- [$^3$H]3-PPP Binding: Membrane preparation obtained from rat whole brain, (+)-[$^3$H]3-PPP and the test drug were allowed to react in 50 mM Tris-HCl buffer (pH 8.0) at 21° C. for 90 minutes.

(2) (−)-[$^3$H]Sulpiride binding: Membrane preparation obtained from rat striatal region, (−)-[$^3$H]sulpiride and the test drugs were allowed to react in 50 mM Tris-HCl buffer (pH 7.7) at 37° C. for 10 minutes.

(3) $^3$H]Phencyclidine binding: Membrane preparation obtained from rat whole brain, [$^3$H]phenycylidine and the test drugs were allowed to react in 5 mM Tris-HCl buffer (pH 7.7) at 25° C. for 2 hours.

After completion of each reaction, the reaction solution was filtered by suction through a glass filter (GF/B) and ratioactivity on the filter was measured by liquid scientillation spectrometry.

Non-specific bindings of (+)-[$^3$H]3-PPP, (−)-$^3$H]sulpiride and [3H]phencyclidine were defined as the bindings obtained by the reactions in the presences of 10 μM (+)-3-PPP, 10 μM (-)-sulpiride and 10 μM phencyclidine, respectively. Specific binding was defined as total binding minus non-specific binding. A constant concentration of [$^3$H]labelled ligand is allowed to react with different concentrations of the test drug under the conditions described in the above (1) to (3) to give an inhibition curve, from which the concentration $IC_{50}$) of the test drug required to produce 50% inhibition of the binding was determined. Results are shown in Table 1.

TABLE 1

| Test drug | Sigma | D$_2$ | Phencyclidine |
|---|---|---|---|
| A | 891.0 ± 12.8 | 44300 | >10000 |
| B | 1024 ± 131.2 | 23200 | >10000 |
| C | 4.8 ± 1.0 | 14300 | >10000 |
| 3-PPP | 24.3 ± 2.9 | — | — |
| Rimcazole | 1460 ± 235 | 86000 | >2000000 |

[The values are $IC_{50}$ value (nM)]
(Note 1)
A: 4-(Di-n-propylaminomethyl)carbazole hydrochloride
B: 5,8-Dimethyl-4-(di-n-propylaminomethyl)carbazole hydrochloride
C: 5,8-Dimethyl-4-(2-di-n-propylaminoethyl)carbazole hydrochloride
(Note 2)
The values of rimcazole are those described in J. Erp. Pharmaco., vol. 155, page 345 (1988), and the values of D$_2$ receptor are those for [$^3$H]spiporone binding.

EXPERIMENT 2

[inhibition of Methamphetamine induced Hyperlocomotion]

Thirty male ICR mice weighing 20 to 35 g were used for each group (5 animals per test, and 6 tests). Mice were placed in the measuring cages, adapted for 60 minutes, and given intraperitoneally the test drugs in Table 1 suspended in 5% gum arabic solution in a dose of 50 mg/kg (0.1 ml/10 g of the body weight). Thirty-five minutes later, methamphetamine dissolved in physiological saline solution was given intraperitoneally in a dose of 1 mg/kg. Fifteen minutes later, the locomotor content was measured for 30 minutes using an Animex apparatus. Control group was given 5% gum arabic only in a similar manner, and seaved for measurement. Results are expressed as percentage to control group in Table 2.

TABLE 2

| Test drug | % to control group |
|---|---|
| A | 39.7** |
| B | 46.6** |
| C | 35.3** |
| Rimcazole | 51.4** |

**$P < 0.01$ (Dunnett's test)
(Note)
A: 4-(Di-n-propylaminomethyl)carbazole hydrochloride
B: 5,8-Dimethyl-4-(di-n-propylaminomethyl)carbazole hydrochloride
C: 5,8-Dimethyl-4-(2-di-n-propylaminoethyl)carbazole hydrochloride The present invention is illustrated by the following examples in more detail.

EXAMPLE 1

Preparation of 5,8-dimethyl-4-(di-n-propyl-aminomethyl)carbazole hydrochloride (1) A mixture of 13.24 g of ethyl indole-4-carboxylate, 15.98 g of acetonylacetone and 13.31 g of p-toluenesulfonic acid monohydrate in 50 ml of ethanol was refluxed for 10 hours. The ethanol was evaporated under reduced pressure, the residue was chromatographed on silica gel column with hexane - ethyl acetate (9 : 1) to give 7.45 g of ethyl 5,8-dimethylcarbazole-4-carboxylate.

m.p. 149.1° C. (recrystallized from isopropyl ether - hexane)

(2) To a suspension of 1.47 g of 60% sodium hydride (in a oil) in 35 ml of dry N,N-dimethylformamide was added dropwise over a 30 minutes period a solution of 7.00 g of ethyl 5,8-dimethylcarbazole-4-carboxylate obtained above in 35 ml of dry N,N-dimethylformamide, and the mixture was stirred for a further 30 minutes. To the mixture was added dropwise a solution of 6.99 g of p-toluenesulfonyl chloride in 35 ml of dry N,N-dimethyl-formamide, and the mixture was stirred further overnight. The reaction solution was poured into ice water and extracted with ethyl acetate, and the organic layer was washed, in turn, with dilute hydrochloric acid, a saturated aqueous sodium bicarbonate solution and a saturated aqueous sodium chloride solution, and dried over anhydrous magnesium sulfate. The solvent was evaporated, and the residue was chromatographed on silica gel column with hexane - ethyl acetate (9 : 1) to give 7.40 g of ethyl 5,8-dimethyl-9-p-toluenesulfonylcarbazole-4- carboxylate.

m.p. 148.6° C. (recrystallized from dichloro-methane - hexane)

(3) To a suspension of 882 mg of aluminum lithium hydride in 35 ml of dry tetrahydrofuran was added dropwise with ice cooling over an hour period a solution of 7.0 g of ethyl 5,8-dimethyl-9-p-toluenesulfonyl-carbazole-4-carboxylate obtained above in 80 ml of dry tetra-hydrofuran, and the mixture was stirred with ice cooling for a further one hour. To the mixture was added dropwise with cooling a saturated aqueous sodium sulfate solution until evolution of hydrogen ceased. The precipitated solid was separated by filtration, and the solvent in the filtrate was evaporated under reduced pressure. The residue was dissolved in 80 ml of N,N-dimethylformamide, after which 10.04 g of carbon tetrachloride and 4.17 g of triphenylphosphine were added in turn, and the mixture was stirred at room temperature overnight. The reaction solution was poured into ice water and extracted with ethyl acetate, and the organic layer was washed, in turn, with dilute hydrochloride, a saturated aqueous sodium bicarbonate solution and a saturated aqueous sodium chloride solution, and dried over anhydrous magnesium sulfate. The solvent was evaporated, and the residue was chromatographed on silica gel column with hexane -dichloromethane (2 : 1) to give 5.63 g of 4-chloromethyl-5,8-dimethyl-9-p-toluenesulfonylcarbazole.

m.p. 148.8° C. (recrystallized from dichloro-methane - isopropyl ether)

(4) A solution of 800 mg of 4-chloromethyl-5,8- dimethyl-9-p-toluenesulfonylcarbazole and 1.02 g of di-n-propylamine in 1 ml of toluene was heated at 90 to 100° C. for 6 hours. After cooling to room temperature, the reaction solution was poured into a 1N aqueous sodium hydroxide solution and extracted with toluene. The organic layer was washed, in turn, with a 1N aqueous sodium hydroxide solution, water and a saturated aqueous sodium chloride solution and dried over anhydrous magnesium sulfate. The anhydrous magnesium sulfate was removed by filtration, and the solvent was evaporated under reduced pressure. To the residue were added 15 ml of ethanol and 5 ml of a 30% aqueous sodium hydroxide solution, and the mixture was refluxed for 13 hours. After evaporation of the solvent under reduced pressure, the residue was extracted with ethyl acetate, and the organic layer was washed, in turn, with water and a saturated aqueous sodium chloride solution and dried over anhydrous magnesium sulfate. The anhydrous magnesium sulfate was removed by filtration, a 4M hydrogen chloride - ethyl acetate solution was added dropwise, the solvent was evaporated under reduced pressure, and the residue was recrystallized from ethanol to give 440 mg of 5,8-dimethyl-4-(di-n-propylaminomethyl)carbazole hydrochloride m.p. 226.7° C.

EXAMPLE 2

Preparation of 5,8-dimethyl-4-(2-di-n-propyl-aminoethyl)carbazole hydrochloride (1) A mixture of 5.39 g of 4-chloromethyl-5,8-dimethyl-9-p-toluenesulfonylcarbazole obtained in Example 1(3), 1.82 g of potassium cyanide and 1.79 g of 18-crown-6 in 80 ml of acetonitrile was stirred at room temperature overnight. The reaction solution was poured into ice water and extracted with ethyl acetate, and the organic layer was washed, in turn, with a saturated aqueous sodium bicarbonate solution and a saturated aqueous sodium chlorided solution and dried over anhydrous magnesium sulfate. Evaporation of the solvent gave 5.21 g of 4-cyanomethyl-5,8-dimethyl-9-p-toluenesulfonylcarbazole.

m.p. 146.3° C. (recrystallized from dichloro-methane - isopropyl ether)

(2) 5.10 g of 4-cyanomethyl-5,8-dimethyl-9-p-toluensulfonylcarbazole in a mixture of 100 ml of a 20% aqueous sodium hydroxide solution and 100 ml of ethanol was refluxed for 18 hours. The reaction solution was concentrated under reduced pressure to about 50 ml, and 50 ml of water was added. The aqueous layer was washed with ethyl ether, and adjusted to pH 3 -4 by addition of concentrated hydrochloric acid, then the formed crystals were collected by filtration and dried. m.p. 185.1° C. (decomposition)

(3) To a solution of 1.15 g of the crystals obtained in the above (2) and 659 mg of N-methylmorpholine in 75 ml of dry tetrahydrofuran was added dropwise with ice cooling 890 mg of isobutyl chloroformate. After stirring for 20 minutes, 719 mg of di-n-propylamine was added, and the mixture was stirred with ice cooling for 2 hours then at room temperature overnight. The reaction solution was poured into ice water and extracted with ethyl acetate, and the organic layer was washed, in turn, with dilute hydrochloric acid, a saturated aqueous sodium bicarbonate solution and a saturated aqueous sodium chloride solution and dried over anhydrous magnesium sulfate, after which the solvent was evaporated under reduced pressure.

A solution of the residue obtained above in 20 ml of dry tetrahydrofuran was added to a suspension of 2.25 g of aluminum lithium hydride in 100 ml of dry tetrahydrofuran, and the mixture was refluxed for 4 hours. The reaction solution was cooled on ice, and a saturated aqueous sodium sulfate solution was added dropwise until evolution of hydrogen ceased. The precipitated solid was collected by filtration, and the solvent in the filtrate was evaporated under reduced pressure. The residue was chromatographed on silica gel column with hexane - acetone (3 : 1), and the desired fractions were combined. After evaporation of the solvent under reduced pressure, the residue was dissolved in ethanol, and a 4M hydrogen chloride - ethyl acetate solution was added dropwise. The solvent was evaporated under reduced pressure, and the residue was recrystallized from ethanol to give 872 mg of 5,8-dimethyl-4-(2-di-n-propylaminoethyl)carbazole hydrochloride.

m.p. 241.0° C.

In a similar manner, there were obtained the following compounds.

5,8-Dimethyl-4-(2-pyrrolidinoethyl)carbazole hydrochloride, m.p. 270.1° C. (recrystallized from ethanol)

5,8-Dimethyl-4-(2-piperidinoethyl)carbazole hydrochloride, m.p. 249.5° C. (recrystallized from ethanol)

5,8-Dimethyl-4-(2-piperazinoethyl)carbazole hydrochloride, m.p. 290.0° C. (decomposition) (recrystallized from methanol)

5,8-Dimethyl-4-(2-morpholinoethyl)carbazole hydrochloride, m.p. 259.6° C. (recrystallized from ethanol)

5,8-Dimethyl-4-(2-di-isopropylaminoethyl)-carbazole hydrochloride, m.p. 275.0° C. (recrystallized from ethanol)

5,8-Dimethyl-4-(2-di-n-hexylaminoethyl)carbazole oxalate, m.p. 164.4° C. (recrystallized from isopropanol)

5,8-Dimethyl-4-[2-(N-benzyl-N-n-propylamino)-ethyl]carbazole hydrochloride, m.p. 182.3° C. (recrystallized from ethanol)

5,8-Dimethyl-4-[2-(N-phenethyl-N-n-propylamino)-ethyl]carbazole hydrochloride, m.p. 194.1° C. (recrystallized from ethanol)

5,8-Dimethyl-4-[2-(N-n-propylamino)-ethyl]carbazole hydrochloride, m.p. 235.3° C. (recrystallized from ethanol)

5,8-Dimethyl-4-(2-n-propylaminoethyl)carbazole hydrochloride, m.p. 253.4° C. (recrystallized from ethanol)

5,8-Dimethyl-4-(2-aminoethyl)carbazole hydrochloride, m.p. 279.3° C. (recrystallized from methanol)

EXAMPLE 3

Preparation of 4-(di-n-propylaminomethyl)-carbazole hydrochloride (1) A mixture of 52.56 g of methyl indole-4-carboxylate, 51.55 g of 2,5-dimethoxytetrahydrofuran and 28.53 g of p-toluenesulfonic acid monohydrate in 300 ml of methanol was refluxed for 10 hours. Then, following a treatment similar to that of Example 1(1), there was obtained 9.14 g of methyl carbazole-4-carboxylate.

m.p. 84.3° C. (recrystallized from dichloromethane - hexane)

(2) Following treatments similar to those of Example (2)-(4) starting from methyl carbazole-4-carboxylate, there was obtained 4-(di-n-propylaminomethyl)carbazole hydrochloride.

m.p. 204.4° C. (recrystallized from ethanol).

EXAMPLE 4

Preparation of 4-(2-di-n-propylaminoethyl)-carbazole hydrochloride

Following treatments similar to those of Example 2(1)-(3) starting from methyl carbazole-4-carboxylate, there was obtained 4-(2-di-n-propylaminoethyl)carbazole hydrochloride.

m.p. 218.0° C. (recrystallized from ethanol)

EXAMPLE 5

Preparation of 5,8-dimethyl-4-(2-di-n-propyl-aminoethyl)carbazole hydrochloride (Another method of Example 2)

To 4.6 g of 4-(2-di-n-propylaminoethyl)indole fumarate were added 30 ml of a 1N aqueous sodium hydroxide solution and 30 ml of ethyl acetate, and the mixture was stirred until the crystals were dissolved. The organic layer was collected, washed, in turn, with a 1N aqueous sodium hydroxide solution, water and a saturated aqueous sodium chloride solution and dried over anhydrous magnesium sulfate, after which the solvent was evaporated under reduced pressure. To the residue were added 2.19 g of acetonylacetone, 4.86 g of p-toluenesulfonic acid monohydrate and 13 ml of ethanol, and the mixture was refluxed for 15 hours. The reaction solution was poured into ice water and extracted with ethyl acetate, and the organic layer was washed, in turn, with a 10% aqueous sodium carbonate solution, water and a saturated aqueous sodium chloride solution and dried over anhydrous magnesium sulfate, after which the solvent was evaporated under reduced pressure. The residue was dissolved in ethanol, a 4M hydrogen chloride - ethyl acetate solution was added, and the formed crystals were collected by filtration and recrystallized from ethanol to give 3.00 g of 5,8-dimethyl-4-(2-di-n-propylaminoethyl)carbazole hydrochloride.

m.p. 241.0° C.

EXAMPLE 6

Preparation of 5,8,9-trimethyl-4-(2-di-n-propylaminoethyl)carbazole hydrochloride To a suspension to 0.25 ml of 60% sodium hydride (in an oil) in 5 ml of dry N,N-dimethylformamide was added dropwise a solution of 2 g of 5,8-dimethyl-4-(2-di-n-propylaminoethyl)carbazole in 10 ml of dry N,N-dimethyl-formamide, and the mixture was stirred for 30 minutes. To the mixture was added dropwise 1.0 g of methyl iodide, and the mixture was stirred at room temperature for 30 minutes. The reaction solution was poured into ice water and extracted with methylene chloride, and the organic layer was dried over anhydrous magnesium sulfate. After evaporation of the solvent, the residue was chromato-graphed on silica gel column with hexane - acetone (1 : 3) to give 5,8,9-trimethyl-4-(2-di-n-propylaminoethyl)-carbazole, to which a 4N hydrochloric acid - ethyl acetate solution was added. The formed crystals were collected by filtration to give 1.7 g of 5,8,9-trimethyl-4-(2-di-n-propylaminoethyl)carbazole hydrochloride.

m.p. 133.1° C. (recrystallized from acetone -hexane)

In a similar manner, there were obtained the following compounds.

9-Acetyl-5,8-dimethyl-4-(2-di-n-propylamino-ethyl)carbazole hydrochloride, m.p. 143.2° C. (recrystallized from ethanol)

9-Benzoyl-5,8-dimethyl-4-(2-di-n-propylamino-ethyl)-carbazole, m.p. 123.0° C. (recrystallized hexane)

What we claimed is:

1. A carbazole compound represented by the formula

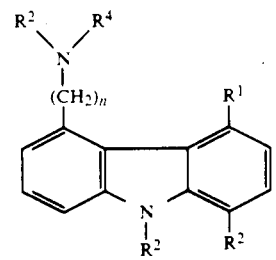

wherein $R^1$ is a hydrogen atom or an alkyl group having 1 to 5 carbon atoms, $R^2$ is a hydrogen atom, an alkyl group having 1 to 5 carbon atoms, an alkanoyl group having 2 to 6 carbon atoms or a benzoyl group, $R^3$ and $R^4$ are the same or different, and are each a hydrogen atom, an alkyl group having 1 to 7 carbon atoms, an alkenyl group having 2 to 4 carbon atoms, an alkyl group having 1 to 3 carbon atoms substitued by a phenyl group, or $R^3$ and $R^4$ together with the nitrogen atom to which they are attached form a morpholino group, a piperidino group, a pyrrolidino group or a piperazino group, and n is an integer from 1 to 3, or a salt thereof.

2. A carbazole compound according to claim 1 which is 5,8-dimethyl-4-(di-n-propylaminomethyl)carbazole hydrochloride.

3. A carbazole compound according to claim 1 which is 5,8-dimethyl-4-(2-di-n-propylaminoethyl)carbazole hydrochloride.

* * * * *

UNITED STATES PATENT AND TRADEMARK OFFICE
CERTIFICATE OF CORRECTION

PATENT NO. : 5,116,995
DATED : May 26, 1992
INVENTOR(S) : NAKAZATO et al

Page 1 of 5

It is certified that error appears in the above-identified patent and that said Letters Patent is hereby corrected as shown below:

Col. 1, the formula at lines 37+, which reads:

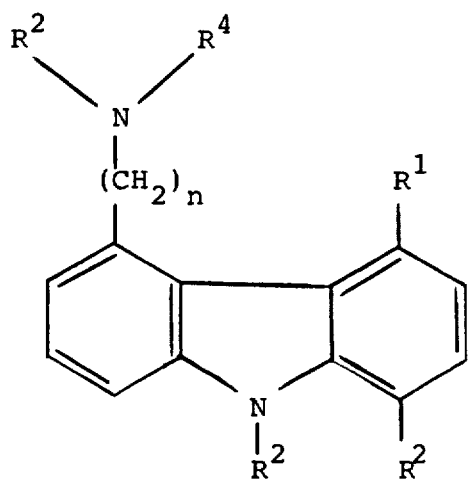

UNITED STATES PATENT AND TRADEMARK OFFICE
CERTIFICATE OF CORRECTION

PATENT NO. : 5,116,995
DATED : May 26, 1992
INVENTOR(S) : NAKAZATO et al

It is certified that error appears in the above-identified patent and that said Letters Patent is hereby corrected as shown below:

should read:

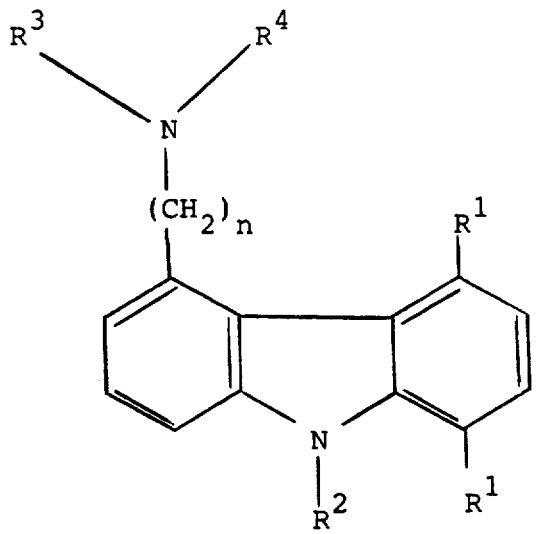

UNITED STATES PATENT AND TRADEMARK OFFICE
CERTIFICATE OF CORRECTION

PATENT NO. : 5,116,995

DATED : May 26, 1992

INVENTOR(S) : NAKAZATO et al

It is certified that error appears in the above-identified patent and that said Letters Patent is hereby corrected as shown below:

Col. 3, line 52, after "II" insert --, which is--.

Col. 5, line 1, delete "triphenylphesphine" and insert --triphenylphosphine--;

line 66, delete "Phosphorus" insert --phosphorus--.

Col. 6, line 35, delete "porposes" insert --purposes--;

line 37, delete "carries" insert --carriers--;

line 44, delete "prectices" insert --practices--;

line 56, delete "Tor" insert --For--; and line 66, delete "discase" insert --disease--.

Col. 7, line 31, "$(-)-^3H]sul-$" should read --$(-)-[^3H]sul-$ --;

line 32, "[3H]" should read --$[^3H]$--.

UNITED STATES PATENT AND TRADEMARK OFFICE
CERTIFICATE OF CORRECTION

PATENT NO. : 5,116,995
DATED : May 26, 1992
INVENTOR(S) : NAKAZATO et al

Page 4 of 5

It is certified that error appears in the above-identified patent and that said Letters Patent is hereby corrected as shown below:

Col. 9, line 62, "tolueen-" should read --toluene- --.

Col. 12, the formula at lines 30-40 which reads:

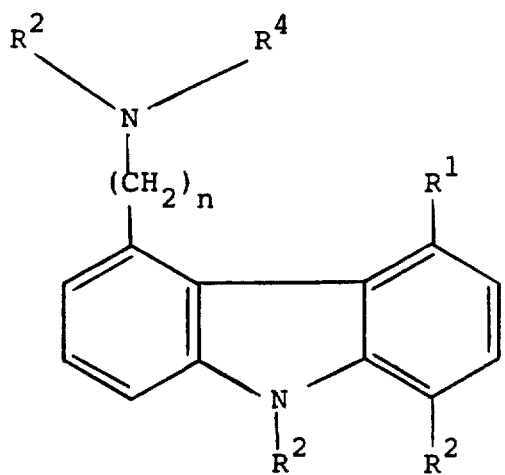

UNITED STATES PATENT AND TRADEMARK OFFICE
CERTIFICATE OF CORRECTION

PATENT NO. : 5,116,995
DATED : May 26, 1992
INVENTOR(S) : Nakazato, et. al.

It is certified that error appears in the above-indentified patent and that said Letters Patent is hereby corrected as shown below:

should read:

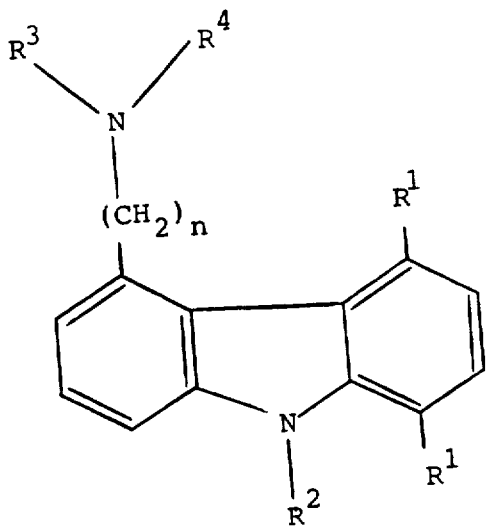

Signed and Sealed this

Nineteenth Day of October, 1993

Attest:

BRUCE LEHMAN

Attesting Officer          Commissioner of Patents and Trademarks